United States Patent [19]

Tang

[11] Patent Number: 4,492,656
[45] Date of Patent: Jan. 8, 1985

[54] DICYANOMETHYL ETHYL PEROXY DICARBONATE POLYMERIZATION INITIATORS

[75] Inventor: Robert H. Tang, Norton, Ohio

[73] Assignee: PPG Industries, Inc., Pittsburgh, Pa.

[21] Appl. No.: 430,167

[22] Filed: Sep. 30, 1982

[51] Int. Cl.³ .......................................... C07C 179/20
[52] U.S. Cl. ............................. 260/453 RZ; 260/463
[58] Field of Search ...................... 260/453 RZ, 463

[56] References Cited

U.S. PATENT DOCUMENTS

| | | | |
|---|---|---|---|
| 2,307,679 | 1/1943 | Hechenbleikner | 260/464 |
| 2,370,588 | 2/1945 | Strain | 260/453 |
| 2,517,964 | 8/1950 | Bissinger | 260/453 |
| 3,022,281 | 2/1962 | Smith | 260/92.8 |
| 3,108,093 | 10/1963 | Pajaczkowski et al. | 260/89.5 |
| 3,636,036 | 1/1972 | Ugi | 260/465 H |
| 3,657,311 | 4/1972 | D'Angelo | 260/463 |

FOREIGN PATENT DOCUMENTS

| | | | |
|---|---|---|---|
| 2021327 | 11/1971 | Fed. Rep. of Germany | 260/453 RZ |
| 1171115 | 1/1959 | France | 260/453 RZ |
| 2087973 | 2/1972 | France | 260/453 RZ |
| 40-6449 | 3/1965 | Japan | 260/453 RZ |

OTHER PUBLICATIONS

"Esters of Peroxycarbonic Acids", by F. Strain et al., J. Am. Chem. Soc., 72, 1254 pp., 1950.
"Fungicidal N-(3,5-dihalophenyl)Carbamates", F. Akira et al., CA, 76:59186n, (1972), Ger. Offen. No. 2,021,327.
"N-Phenylcarbamates," CA, 77:88111k, (1972), Fr. Demande No. 2087973.
"α-Cyanoisopropyl Ester of Chloroacetic Acid", by V. P. Kondratenko, et al., CA, 65:16871d, (1966), U.S.S.R. No. 182,134.

*Primary Examiner*—Henry R. Jiles
*Assistant Examiner*—Robert C. Whittenbaugh
*Attorney, Agent, or Firm*—Irwin M. Stein

[57] ABSTRACT

Organic peroxydicarbonates represented by the following graphic formula are described.

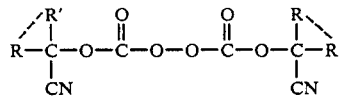

In the formula, R and R' are each selected from an alkyl group containing from 1 to 4 carbon atoms, a cycloalkyl group of from 5 to 7 carbon atoms, a $C_1$–$C_4$ alkyl substituted cycloalkyl group, or participate in a cycloalkyl group having from 5 to 7 carbon atoms, provided that when one of R and R' is cycloalkyl, the other is alkyl. The peroxydicarbonates are useful as initiators for the polymerization or copolymerization of ethylenically unsaturated monomers or the cross-linking of unsaturated polyester resins. The organic peroxydicarbonates can be used in combination with commercially available peroxydicarbonates, particularly those having a shorter half-life.

4 Claims, No Drawings

DICYANOMETHYL ETHYL PEROXY DICARBONATE POLYMERIZATION INITIATORS

DESCRIPTION OF THE INVENTION

The present invention relates to certain novel peroxydicarbonate compositions and to their use in the polymerization and copolymerization of ethylenically unsaturated monomers, e.g., vinyl chloride. The utility of certain peroxydicarbonate compounds for initiating polymerization reactions is known. See, for example, U.S. Pat. No. 2,370,588 and J. Am. Chem. Soc., 72, 1254 (1950) of Strain et al which discloses generally the preparation of various dialkyl peroxydicarbonates and their use as polymerization initiators. See also, Dunn et al, U.S. Pat. No. 2,843,576 and Marous et al, U.S. Pat. No. Re. 25,763.

Dialkyl peroxydicarbonate are generally used as low temperature free-radical polymerization initiators (and curing agents), the more common dialkyl peroxydicarbonates having a ten hour half-life (in benzene) of between about 35° C. and 50° C. The stability of dialkyl peroxydicarbonates at room temperature, i.e. the shelf life of such percarbonates at room temperature, is not as long as less reactive peroxides because of their activity at relatively low temperatures. Consequently, dialkyl peroxydicarbonates such as diisopropyl-, di-n-propyl- and di-secondary butyl peroxydicarbonates are shipped as frozen solids or as diluted or undiluted liquids under refrigeration. While the use of such peroxydicarbonates requires special handling techniques for shipment and storage, i.e., refrigeration, their use is preferred for many polymerizations for the reasons that they are more efficient at the polymerization temperatures utilized than the less reactive organic peroxides, such as lauroyl peroxide and dibenzoyl peroxide. Consequently use of these peroxydicarbonates results in shorter polymerization times per batch of polymer produced.

Attempts have been made to reduce the rate of self-induced homolytic decomposition of dialkyl peroxydicarbonates, i.e., improve their shelf life under non-refrigerative storage conditions, by increasing the size of the organic radical at the terminal ends of the peroxydicarbonate molecule. For example, U.S. Pat. No. 3,720,700 describes the chemical compound, dicetyl peroxydicarbonate, which is reported to have superior storage stability compared with peroxydicarbonates such as diisopropyl peroxydicarbonate. U.S. Pat. No. 4,137,252 describes dicyclododecyl peroxydicarbonate which is reported to be stable at room temperature. The patent reports that dicyclododecyl peroxydicarbonate loses only 6.6 percent of its assay when stored for three weeks at a temperature of 30° C. U.S. Pat. No. 3,799,966 describes the compound di(2-phenoxyethyl) peroxydicarbonate, which is reported as being stable at 50° C. with little or no loss of assay.

While the aforesaid high molecular weight peroxydicarbonates are reported to be more stable at room temperature than the more common normally liquid, i.e., liquid at room temperature (20° C.), peroxydicarbonates, they possess a low percent active oxygen (per unit molecular weight) relative to the normally liquid peroxydicarbonates because of their higher molecular weight. For example, dicetylperoxydicarbonate has a value of 2.8% active oxygen; whereas disecondarybutyl peroxydicarbonate has a value of 6.8% active oxygen. There is, therefore, a continuing need for peroxydicarbonates which have improved storage stability at room temperature relative to the normally liquid peroxydicarbonates but yet possess a relatively high percent active oxygen.

It has now been discovered that organic peroxydicarbonates represented by the following graphic formula I possess desirable properties of improved shelf life at room temperature and a relatively high percent active oxygen.

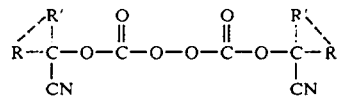

In the formula, R and R' are each selected from the group consisting of $C_1$–$C_4$ alkyl, $C_5$–$C_7$ cycloalkyl, $C_1$–$C_4$ alkyl substituted $C_5$–$C_7$ cycloalkyl or participate in a cycloalkyl group having from 5 to 7 carbon atoms (as shown by the broken line connecting R and R'), provided that when one of R and R' is a $C_5$–$C_7$ cycloalkyl, the other is a $C_1$–$C_4$ alkyl. The aforesaid described peroxydicarbonates are solids at room temperature and consequently can be stored at such temperature for short periods of time, e.g., less than 30 days without refrigeration. However, from the evidence at hand, it is possible for these peroxydicarbonates to undergo sudden homolytic decomposition if allowed to remain at room temperature for extended periods. Therefore, at the present time, it is recommended that storage temperatures less than room temperature be employed.

Further, the half life of such peroxydicarbonates at 50° C. (as measured in benzene) is longer than the corresponding half life of more common normally liquid dialkyl peroxydicarbonates, such as di-secondarybutyl peroxydicarbonate. For example, the compound di(1-cyano-1-methylethyl) peroxydicarbonate has a half life at 50° C. (measured in benzene) of about 9.5 hours as contrasted with 2.3 hours for di-secondarybutyl peroxydicarbonate.

The peroxydicarbonates represented by graphic formula I can be employed for the polymerization and copolymerization of ethylenically unsaturated monomers. Illustrative of such monomers include, but are not limited to, vinyl aromatic compounds such as styrene and p-chlorostyrene; esters of aliphatic alpha-methylene monocarboxylic acids such as methyl methacrylate, n-butyl acrylate, and ethyl acrylate, vinyl esters such as vinyl acetate; vinyl halides, e.g., vinyl chloride; vinyl ethers, e.g., vinyl methylethers; vinylidene halides such as vinylidene chloride, and alpha-ethylenically unsaturated hydrocarbons, such as ethylene and propylene, as well as for the cross-linking of unsaturated polyester resins. The polymerization of the ethylenically unsaturated monomers can be performed as a suspension, emulsion, solution or bulk polymerization.

DETAILED DESCRIPTION OF THE INVENTION

The present invention relates to novel organic peroxydicarbonates represented by the following graphic formula:

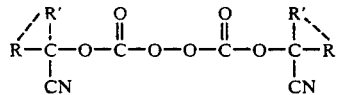

In the above formula I, R and R' are each selected from $C_1$–$C_4$ alkyl, $C_5$–$C_7$ cycloalkyl, $C_1$–$C_4$ alkyl substituted $C_5$–$C_7$ cycloalkyl or participate in a cycloalkyl group of from 5 to 7 carbon atoms (as shown by the broken line connecting R and R'). When one of R and R' is a cycloalkyl group, the other of R and R' is an alkyl group. Preferably, R and R' are each a $C_1$–$C_2$ alkyl group or together participate to form a cyclohexyl group. Illustrative of the peroxydicarbonates within the scope of formula I are: di(1-cyano-1-methylethyl)peroxydicarbonate, di(1-ethyl-1-cyanoethyl)peroxydicarbonate, di(1-cyano-1-ethyl-n-propyl)peroxydicarbonate, di(1-cyano-1-methyl-n-propyl)peroxydicarbonate, di(1-cyano-1-cyclohexylethyl)peroxydicarbonate, di(1-cyano-1-cyclohexyl)peroxydicarbonate, di(1-cyano-1-cyclopentyl)peroxydicarbonate, di(1-cyano-1-cycloheptyl) peroxydicarbonate, di(1-cyano-1-methylcyclohexyl)peroxydicarbonate and di(1-cyano-1-t-butylcyclohexyl) peroxydicarbonate. The preferred peroxydicarbonates are 1-cyano-1-methylethyl peroxydicarbonate and di(1-cyano-1-cyanohexyl)peroxydicarbonates.

The peroxydicarbonates of formula I can be prepared from the chloroformate of the corresponding dialkyl cyanohydrin using known techniques for the manufacture of symmetrical peroxydicarbonates. The aforesaid preparative technique involves the careful reaction of the aforesaid chloroformate with aqueous sodium peroxide at low temperatures, usually less than 20° C., e.g., 0° C.–10° C., and is described in U.S. Pat. No. 2,370,588 and in Volume 72, page 1254 et seq (1950) of the Journal of American Chemical Society.

The chloroformate of the dialkyl cyanohydrin can be prepared by the reaction of the corresponding cyanohydrin with phosgene using well known phosgenation techniques. The cyanohydrin in turn can be prepared by the reaction of the corresponding ketone with hydrocyanic acid at temperatures of from 10° C. to 20° C. using well known techniques such as described for the preparation of acetone cyanohydrin in Organic Synthesis, Vol. II, pp. 7–8, John Wiley and Sons, A. H. Blatt, Ed., New York, 1943.

The synthesis of the peroxydicarbonates of formula I can be depicted by the following three balanced equations in which R and R' are as defined with respect to graphic formula I:

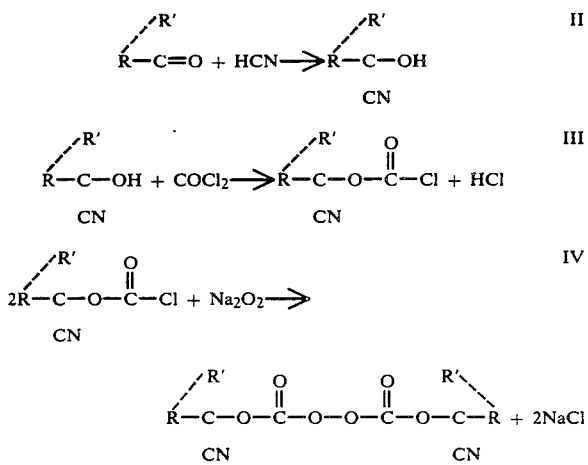

The peroxydicarbonates of the present invention can be used to polymerize ethylenically unsaturated monomers or mixtures thereof. An especially suitable monomer is vinyl chloride, which can be homopolymerized or copolymerized. Typically, vinyl chloride can be copolymerized with up to about 15 percent of another ethylenically unsaturated monomer. Examples of monomers which are co-polymerizable with vinyl chloride include vinylidene chloride, ethylene, propylene and vinyl acetate. Polymerization of the vinyl chloride is accomplished by contacting the vinyl chloride monomer or mixtures of monomers with an initiating amount of the peroxydicarbonate of the present invention under free-radical initiating conditions. Generally from about 0.003 to about 3. e.g., from 0.02 to 0.3, weight percent of the compositions of the present invention, based upon the total weight of monomer polymerized, will be suitable for initiation of the polymerization. The precise amount of peroxydicarbonate used will vary with the monomer(s) to be polymerized and typical levels of initiator required are well known to those skilled in the art. The temperatures at which the polymerizable monomers are polymerized will typically range from about 35° C.–75° C.

The peroxydicarbonates of the present invention can also be used to cure unsaturated polyester resins. Unsaturated polyester resins which can be cured with peroxydicarbonates are well-known to those skilled in that art. Typically between about 0.05 and about 5, e.g., 0.2 to 2.5, parts by weight of the peroxydicarbonates of formula I can be added to 100 parts by weight of the unsaturated polyester resin composition. The resultant mixture is heated at a temperature of from about 20° C. to about 150° C., e.g., 50° C. to 100° C., whereby the resin is cured.

The peroxydicarbonate of the present invention can be used in combination with the normally liquid peroxydicarbonates. For example, the peroxydicarbonates of the present invention can be used in combination with, for example diethyl peroxydicarbonate, diisopropyl peroxydicarbonate, di-n-propyl peroxydicarbonate, di-n-butyl peroxydicarbonate, di-secondary butyl peroxydicarbonate, di-tertiarybutyl peroxydicarbonate, and di-2-ethylhexyl peroxydicarbonate.

When used in combination with the normally liquid peroxydicarbonates, the mole ratio of the peroxydicarbonates of the present invention to that of the normally liquid peroxydicarbonate will typically range from about 0.01:1 to about 10:1, e.g., 1:1.

The present invention is more particularly described in the following Examples which are intended as illustrative only since numerous modifications and variations therein will be apparent to those skilled in the art.

EXAMPLE 1

Preparation of 1-Cyano-1-methylethyl chloroformate

Into a one liter round bottom flask equipped with a phosgene inlet tube, a dry ice cooled condenser, a Teflon blade stirrer and a dropping funnel were added 200 milliliters (ml) of anhydrous ether. The flask was cooled in a dry ice/2-propanol bath and 100 ml of liquid phosgene (1.5 moles) were introduced. A mixture of acetone cyanohydrin (85 grams, 1 mole) and pyridine (80 ml, 1 mole) in 400 ml of anhydrous ether was added dropwise to the pool of phosgene, through the dropping funnel. When the addition was completed, the dry ice/2-propanol bath was replaced by an ice bath and stirring was continued for two hours. The reaction mixture was then stirred at room temperature for an additional two hours. Nitrogen was introduced into the reactor through the reactor inlet tube to remove the excess phosgene. The phosgene containing nitrogen gas stream removed from the reactor was forwarded to a packed column into the top of which was sprayed a solution of 15 weight percent sodium hydroxide and 0.8 weight percent pyridine. After degassing, the reaction mixture was filtered and dried over anhydrous magnesium sulfate. The ether solvent was evaporated and 123 grams (72% yield) of 1-cyano-1-methylethyl chloroformate as a light yellow liquid was obtained. Identification of the product as 1-cyano-1-methylethylchloroformate was confirmed by infrared and nuclear magnetic resonance (NMR) spectroscopy.

EXAMPLE 2

Preparation of Di(1-cyano-1-methylethyl) peroxydicarbonate

Into a 500 ml round bottom flask equipped with a thermometer, a dropping funnel and a Teflon blade stirrer were added a solution of 50 weight percent sodium hydroxide (41.9 grams, 0.52 mole) and 84 grams of distilled water. The solution was cooled to 15° C. by an ice bath and 50% hydrogen peroxide (18.4 grams, 0.27 mole) was added slowly through the dropping funnel. A sodium peroxide slurry formed immediately. The sodium peroxide slurry was transferred slowly into a 500 ml four-necked round bottom reactor flask containing 82.1 grams (0.5 mole) of the 1-cyano-1-methylethyl chloroformate of Example 1. The reactor flask was equipped with a Teflon blade stirrer, a bottom stopcock, a vent, a sodium peroxide slurry inlet and a thermometer. The temperature within the reactor flask was maintained at about 15° C. or less by spraying ice water on the outside of the flask. On completing the addition of the sodium peroxide slurry, 50 ml of distilled water was added to the reactor flask with stirring and a solid material precipitated immediately. The stirring was continued for 90 minutes. Thereafter, the solid precipitate (43.5 grams, 63% yield) was recovered by filtration, washed twice with distilled water and once with 2-propanol. The product was a white solid having a melting point of 58°-59° C. Identification of the product as di(1-cyano-1-methylethyl)peroxydicarbonate was confirmed by infrared and NMR spectroscopy. Iodometric titration of the product gave a percarbonate assay of 93%.

The half-life of di(1-cyano-1-methylethyl)peroxidicarbonate at 50° C. was determined by maintaining separate aliquots of a 1.5 molar benzene solution of the peroxydicarbonate in a constant temperature both maintained at 50±0.1° C. for various time intervals, and analyzing the amount of the peroxydicarbonate remaining in the aliquot after removal from the bath. The half-life was calculated to be 9.5 hours.

EXAMPLE 3

Preparation of 1-cyano-1-cyclohexyl chloroformate 1-cyano-1-cyclohexyl chloroformate was prepared using the procedure of Example 1 by phosgenation of cyclohexanone cyanohydrin. 100 grams (0.8 mole) of cyclohexanone cyanohydrin yielded 144 grams of the chloroformate. Identification of the product was obtained by infrared and NMR spectroscopy.

EXAMPLE 4

Preparation of Di(1-cyano-1-cyclohexyl)peroxydicarbonate

Into a 500 ml round bottom reactor flask equipped as described in Example 2 was added a mixture of the 1-cyano-1-cyclohexyl chloroformate (54.5 grams, ~0.25 mole) of Example 3, 50% hydrogen peroxide (9.3 grams, 0.14 mole), 5 grams of 2-propanol and 28.2 grams of distilled water. The reaction mixture was agitated and cooled to 15° C. and a solution of 50% sodium hydroxide (22.1 grams, 0.26 mole) and 22 grams of distilled water was added dropwise. The reaction was poststirred for 30 minutes after completion of sodium hydroxide addition. The product was washed twice with water and dried with anhydrous magnesium sulfate. 23 grams of a crude colorless liquid having a percarbonate assay of 60% were obtained. The crude product was purified by dissolving it in a mixture of 10 parts by weight of pentane and 1 part of 2-propanol. The solution was stored in a freezer (−25° to −30° C.) for several days. A white precipitate (6.9 grams) was recovered which had a percarbonate assay of 93.4% and a melting point of 51° C.-52° C. Identification of the product as di(1-cyano-1-cyclohexyl)peroxydicarbonate was confirmed by infrared and NMR spectroscopy.

EXAMPLE 5

The peroxydicarbonate of Examples 2 was used to polymerize methyl methacrylate. For purposes of comparison, methyl methacrylate was also polymerized with diisopropyl peroxydicarbonate and di-secondarybutyl peroxydicarbonate. The polymerizations were performed as follows:

About 1 mole percent of the peroxydicarbonate and 200 ml of methylene chloride were charged to 28 oz. pop bottles. 10 grams (1 mole) of methyl methacrylate were added to the bottles and argon bubbled through the mixture for a few minutes to remove atmospheric oxygen from the bottles. The bottles were then capped, sealed and placed in safety cages. The bottles were placed in a constant temperature 50° C. both for 18 hours during which the bottles were tumbled at a rate of 30 revolutions per minute.

A viscous, polymer latex was obtained at the end of the 18 hour polymerization period. Poly(methyl methacrylate) was precipitated by adding methanol to the reaction mixture. The precipitated polymer was collected, washed with methanol and dried in a vacuum oven at 50° C. overnight. The inherent viscosity (0.5 grams/100 ml in methylene chloride, 30° C.) of each product was determined, and the molecular weight estimated from a standard inherent viscosity-molecular weight curve made from poly(methyl methacrylate) of known molecular weight. Results are tabulated in Table I.

TABLE I

| Peroxydicarbonate | Poly(methyl methacrylate) | | |
|---|---|---|---|
| | Yield (grams) | Inh. Viscosity | Molecular Wt. |
| Di-isopropyl | 83 | 0.15 | $72 \times 10^3$ |
| Di-secondarybutyl | 84 | 0.16 | $76 \times 10^3$ |
| Di(1-cyano-1-methylethyl) | 96 | 0.20 | $96 \times 10^3$ |

The data of Table I demonstrate that the peroxydicarbonates of the present invention, e.g., di(1-cyano-1-methylethyl)peroxydicarbonate, are useful as polymerization initiators for ethylenically unsaturated monomers, e.g., methyl methacrylate.

Although the present invention has been described with reference to specific details of certain embodiments thereof, it is not intended that such detail should be regarded as limitations upon the scope of the invention except as and to the extent that they are included in the accompanying claims.

What is claimed is:

1. An organic peroxydicarbonate of the graphic formula:

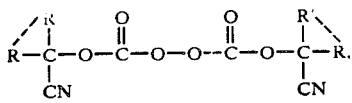

wherein R and R' are each selected from the group consisting of $C_1$–$C_4$ alkyl, $C_5$–$C_7$ cycloalkyl, and $C_1$–$C_4$ alkyl-substituted $C_5$–$C_7$ cycloalkyl, or participate in a cycloalkyl group of from 5 to 7 carbon atoms, provided that when one of R and R' is each individually a cycloalkyl group, the other is a $C_1$–$C_4$ alkyl.

2. An organic peroxydicarbonate in accordance with claim 1 wherein R and R' are each selected from the group consisting of $C_1$–$C_4$ alkyl, cyclohexyl, and $C_1$–$C_4$ alkyl-substituted cyclohexyl, or participate in a cycloalkyl group of from 5 to 7 carbon atoms, provided that when one of R and R' is each individually cyclohexyl or $C_1$–$C_4$ alkyl substituted cyclohexyl, the other is a $C_1$–$C_4$ alkyl.

3. Di(1-cyano-1-methylethyl)peroxydicarbonate.

4. Di(1-cyano-1-cyclohexyl)peroxydicarbonate.

* * * * *

UNITED STATES PATENT AND TRADEMARK OFFICE
CERTIFICATE OF CORRECTION

PATENT NO. : 4,492,656

DATED : January 8, 1985

INVENTOR(S) : Robert H. Tang

It is certified that error appears in the above-identified patent and that said Letters Patent is hereby corrected as shown below:

The formula in Claim 1 should read as follows:

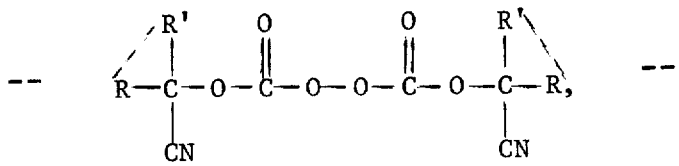

Signed and Sealed this

Twenty-eighth Day of May 1985

[SEAL]

*Attest:*

DONALD J. QUIGG

*Attesting Officer*     *Acting Commissioner of Patents and Trademarks*